United States Patent [19]

Gollobin et al.

[11] Patent Number: 5,330,438
[45] Date of Patent: Jul. 19, 1994

[54] PROTECTIVE SHEATH FOR BUTTERFLY NEEDLES AND IV INFUSION SET AND SHEATH ASSEMBLY

[76] Inventors: Peter J. Gollobin, 54 Woodland Dr., Oyster Bay, N.Y. 11771; Vincent Chimienti, 2 Osborne La., Greenvale, N.Y. 11548

[21] Appl. No.: 133,470

[22] Filed: Oct. 8, 1993

[51] Int. Cl.⁵ .............................................. A61N 5/32
[52] U.S. Cl. .................................... 604/177; 604/110; 604/162
[58] Field of Search ................ 604/165, 177, 110, 162

[56] References Cited

U.S. PATENT DOCUMENTS

| | | | |
|---|---|---|---|
| 4,941,881 | 7/1990 | Masters et al. | 604/177 |
| 5,069,341 | 12/1991 | Barbieri et al. | 604/110 |
| 5,120,320 | 6/1992 | Fayagold | 604/177 |
| 5,192,275 | 3/1993 | Burns | 604/177 |
| 5,219,339 | 6/1993 | Saito | 604/177 |

FOREIGN PATENT DOCUMENTS 425448  5/1991  European Pat. Off. ............ 604/110

Primary Examiner—John G. Weiss
Attorney, Agent, or Firm—Galgano & Burke

[57] ABSTRACT

A protecting sheath for an IV infusion set of the type including a length of tube with a hollow needle at one end, and a pair of outwardly projecting flexible wings adjacent the end of the tubing with the needle is disposed on the tube and adapted to be slid over the needle to cover the needle. The sheath includes a hollow generally tubular body having a forward end oriented toward the needle and a rearward end oriented away from the needle. The body has at least three longitudinally extending fingers separated by slots extending from the forward end of the body toward the rearward end. Each of the slots is dimensioned to receive only one of the wings to allow at least part of sheath to be slid past the wings to cover the needle after use.

20 Claims, 3 Drawing Sheets

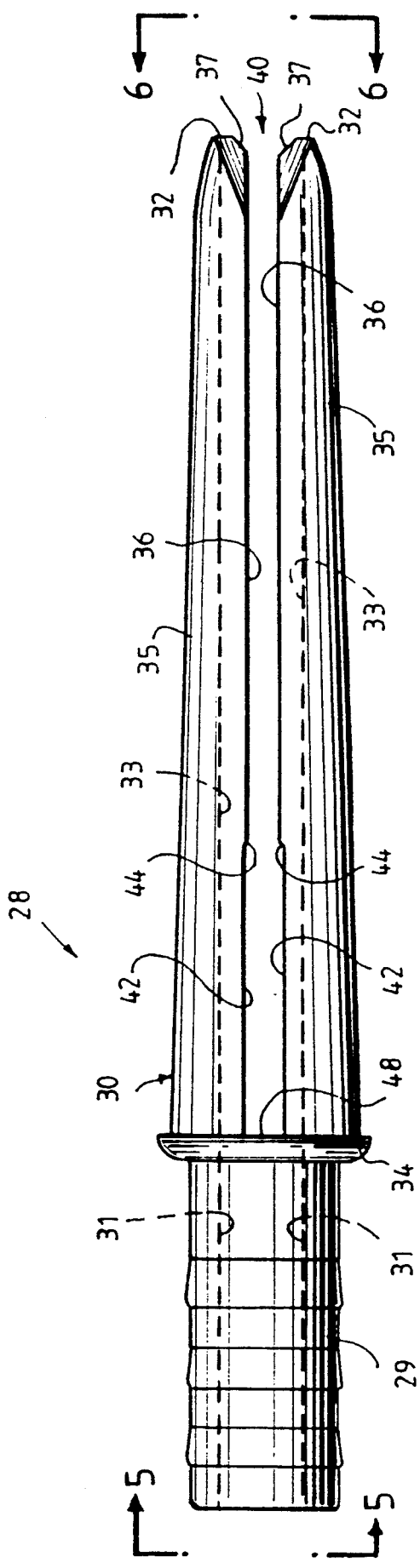
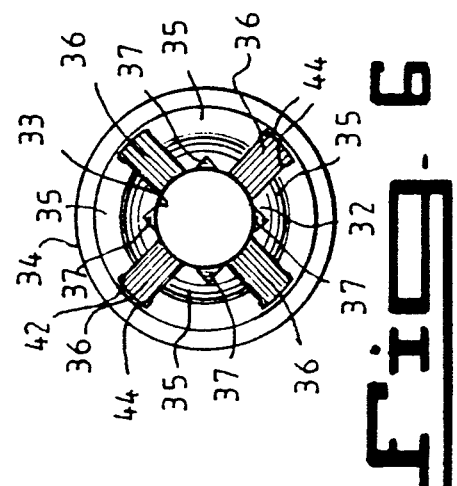
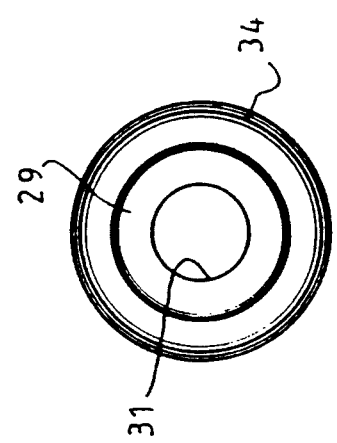

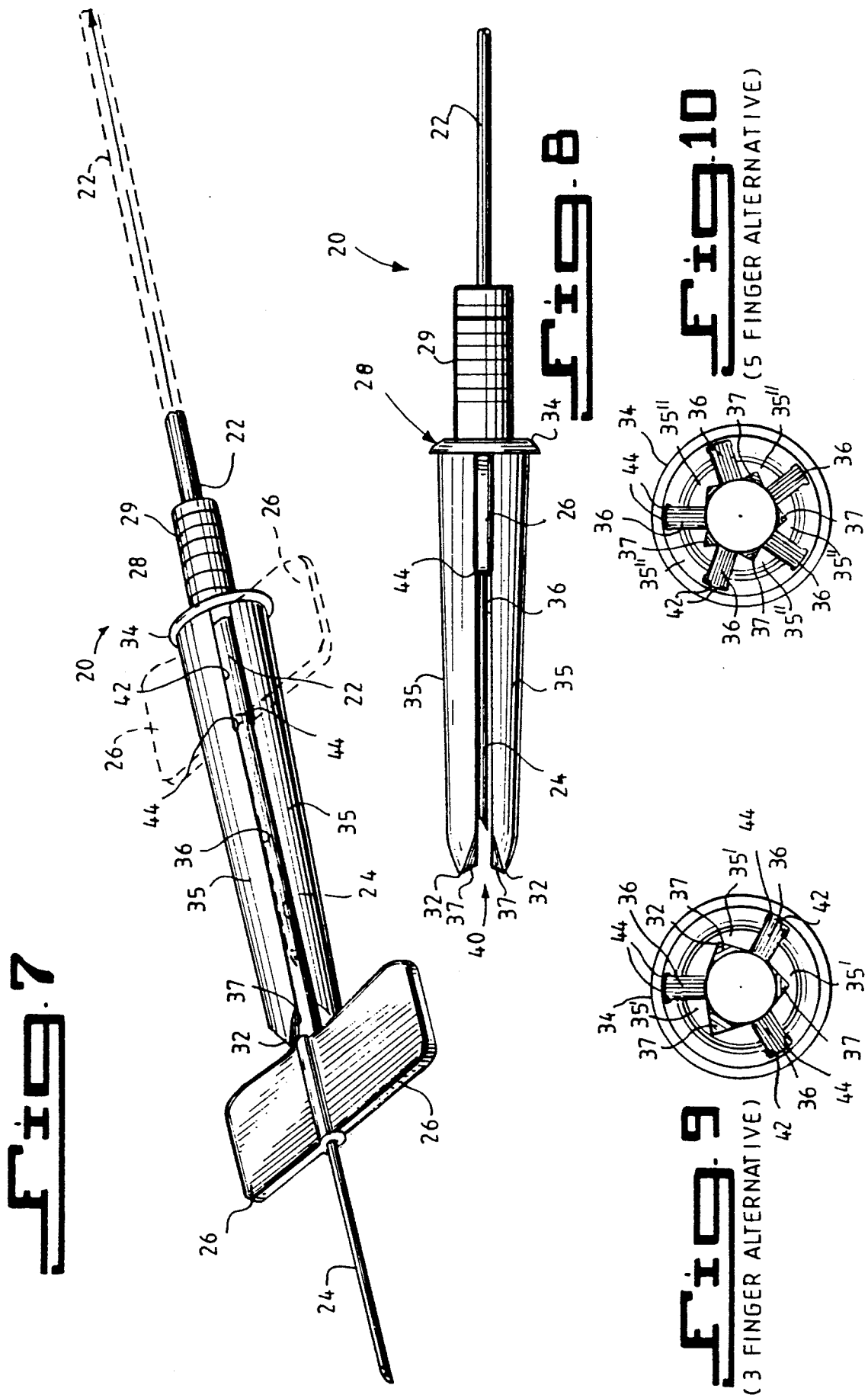

PROTECTIVE SHEATH FOR BUTTERFLY NEEDLES AND IV INFUSION SET AND SHEATH ASSEMBLY

BACKGROUND OF THE INVENTION

1. Field of the Invention

The present invention relates to a protective sheath for butterfly needles and, in particular, to an IV infusion set with a protective sheath to protect accidental needlesticks from such infusion sets.

2. Prior Art

Accidental needlesticks from contaminated medical equipment such as syringes and IV equipment poses serious risks to healthcare professionals. Even maintenance personnel who dispose of the used medical equipment are at risk. Hepatitis, AIDS and other diseases can be, and sometimes are transmitted by accidental needlesticks from needles used on infected patients.

Attempts have been made to combat the problem of accidental needlesticks from syringes. See, for example, the devices disclosed in prior U.S. Pat. Nos. 4,654,034, 4,681,567, 4,740,204 and 4,740,204. Moreover, attempts have been made to specifically prevent needlesticks from IV equipment. See, for example, the devices disclosed in U.S. Pat. Nos. 3,572,334, 4,140,108, 4,160,450, 4,170,993, 4,676,783, 4,781,692, 4,820,282, 4,834,708, 4,846,808, 4,888,001, 4,917,669, 4,935,011, 4,941,881, 4,943,283, 4,969,876, 5,120,320.

In particular, U.S. Pat. No. 4,941,881 discloses an IV infusion set with a sheath which includes a length of tube having a hollow needle at one end of the tube. A sheath is slidably disposed on the tube and is adapted to be slid over the needle to cover the needle after it has been used. The sheath includes means for locking the sheath in its position covering the needle to prevent needlesticks from the used needle. The IV infusion set is of the type having outwardly projecting flexible wings adjacent the needle and the means for locking the sheath preferably comprise means for engaging the wings. The sheath comprises a hollow generally tubular body having a forward end oriented toward the needle and a rearward end oriented away from the needle. The body has one longitudinally extending slot extending from the forward end of the body toward the rearward end. The slot is adapted to receive the wings to allow at least part of the sheath to be slid past the wings to cover the needle. The forward end of the slot widens to a generally V-shaped mouth to facilitate the passage of the wings into the slot. The sheath may include a cutout in the body at the rearward end of the slot for receiving and engaging the wings to lock the body in its position covering the needle.

The present invention provides an improvement to the IV infusion set and sheath disclosed in U.S. Pat. No. 4,941,881 the subject matter of which is incorporated herein by reference thereto. The present invention affords an improved sheath construction which significantly minimizes the possibility of improper operation and jamming of the used needle relative to the sheath during the sheathing operation.

SUMMARY OF THE INVENTION

Accordingly, it is an object of the present invention to provide a novel and improved protective sheath for butterfly needles and an IV infusion set which includes such an improved sheath which covers the needle after it is used in order to reduce the risk of needlesticks with the used needle.

It is a further object of the present invention to provide such a protective sheath and IV infusion set in which the sheath can be locked into position covering the needle by simply pulling on the IV tube whereby the needle is retracted into the protective sheath.

It is a more particular object of the present invention to provide such a protective sheath and IV infusion set which is highly effective in operation, easy and facile to use, economical to fabricate and of relatively simple design.

Certain of the foregoing and related objects are readily attached in an improved IV infusion set of the type including a length of tube with a hollow needle at one end, and a pair of outwardly projecting flexible wings adjacent the end of the tubing with the needle and a sheath slidably disposed on the tube and adapted to be slid over the needle to cover the needle after use. The sheath comprises a hollow generally tubular body having a forward end oriented toward the needle and a rearward end oriented away from the needle. The body has at least three longitudinally extending fingers separated by slots extending from the forward end of the body toward the rearward end, each of the slots being dimensioned to receive only one of the wings to allow at least part of said sheath to be slid past the wings to cover the needle. Preferably, the slots each have a width which is slightly less than the width of one of said wings. Desirably, the sheath includes means for locking the sheath in its position covering the needle to prevent needlesticks from the used needle. Most advantageously, the means for locking the sheath comprising means on the sheath for engaging the wings, specifically a cutout at the rearward end of each of the slots, the cutout being adapted to receive and engage the wings to lock the body in its position covering the needle. The cutout has a width at least equal to the width of one of the wings.

In certain preferred embodiments of the invention, the tubular body has three fingers and three slots, four fingers and four slots, or five fingers and five slots. Most desirably, the protective sheath is made from plastic, and the forward ends of the fingers are V-shaped and tapered to facilitate the passage of the wings into the slots.

Certain of the foregoing and related objects are also attained in a protective sheath for a butterfly type needle having the aforementioned construction.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawings, wherein similar reference characters denote similar elements throughout the several views:

FIG. 4 is an enlarged side elevational view of the protective sheath;

FIG. 5 is an enlarged rear end view of the protective sheath taken along line 5—5 of FIG. 4;

FIG. 6 is an enlarged front elevational view of the protective sheath taken along line 6—6 of FIG. 4;

FIG. 7 is an enlarged perspective view showing the needle and butterfly wings thereof immediately prior to being retracted into the protective sheath and, in phantom view, in a fully retracted and locked state within the protective sheath.

FIG. 8 is an enlarged side elevational view showing the needle and butterfly wings in a fully retracted and locked position with respect to the sheath;

FIG. 9 is an enlarged front elevational view of a three-finger alternative embodiment of the protective sheath; and FIG. 10 is an enlarged front elevational view of a five-finger alternative embodiment of the protective sheath.

BRIEF DESCRIPTION OF THE PREFERRED EMBODIMENTS

Referring now in detail to the drawings, a first embodiment of an improved IV infusion set is indicated generally as 20 in FIGS. 1-8. The IV infusion set 20 is of the type comprising a section of tube 22 preferably made of clear flexible plastic, a hollow needle 24 preferably made of metal and joined to at one end of the tube and two outwardly projecting flexible wings 26 preferably made of flexible plastic. The wings 26 are located adjacent the needle 24. This type of IV infusion set is commonly referred to as a "butterfly" infusion set. As is well known, a connector (not shown in FIGS. 1-8), is disposed on the end of the tube 22 opposite the needle 24 for connecting the IV infusion set to the appropriate medical apparatus.

Figure 1:
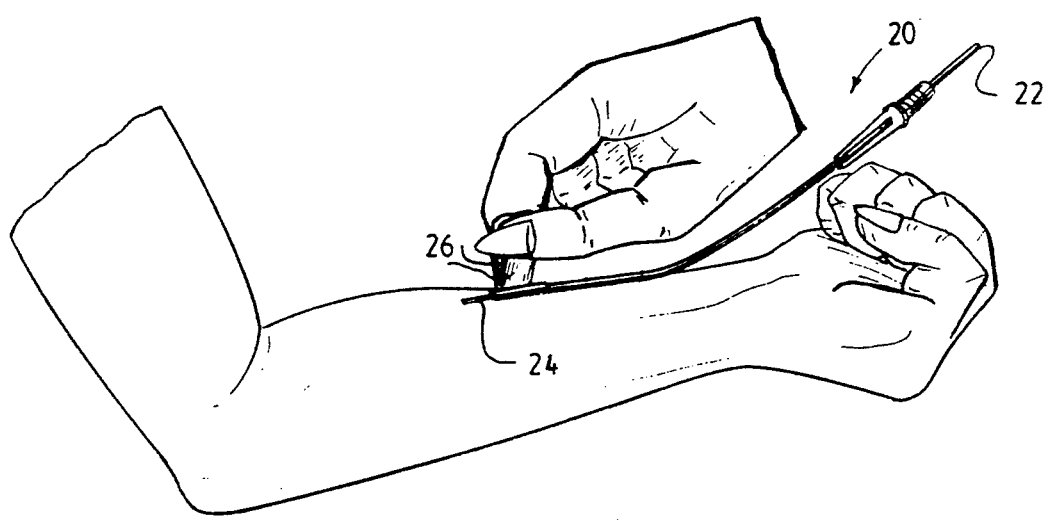
FIG. 1 is a perspective view showing the IV infusion set being inserted, or removed from the forearm of a patient with the protective sheath rearwardly displaced on the needle tube.
Figure 2:
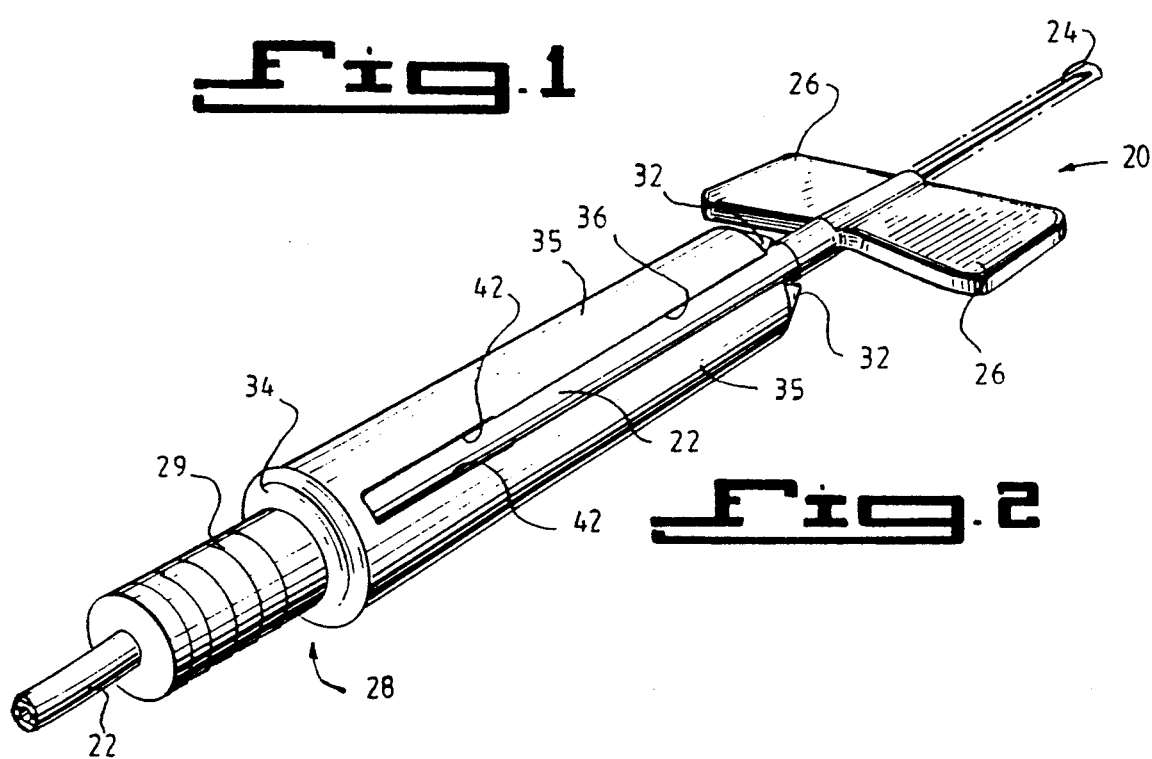
FIG. 2 is an enlarged perspective view of the IV infusion set and sheath showing the needle and butterfly wings immediately prior to retraction into the sheath.

The improved IV infusion set 20 includes a sheath, generally designated by reference numeral 28, slidably disposed on tube 22. Although the sheath 28 is slidably disposed on the tube, before and during use of the infusion set, as shown in FIG. 1, it is initially spaced rearwardly from wings 26 so that it does not interfere with the needle 24 when the IV infusion device is in use. Of course, some means for temporarily securing the sheath 28 relative to the tube 22 could also be used. The sheath 28 is adapted to be slid past the flexible wings 26 to cover the needle after the needle has been used. The sheath 28 includes means for releaseably locking the sheath in its position covering the needle 24. This locking means preferably comprises means on the sheath for engaging the wings 26.

The sheath 28 preferably comprises a knurled, generally cylindrical, annular base 29 by which the sheath may be easily grasped. Base 29 has a central bore 31 through which tube 22 may slidably pass. Base 29 is further integrally joined to a hollow generally tubular body 30 having a forward end 32 oriented toward the needle 24 and a rearward end 34 oriented away from the needle 24 and attached to the annular base 29. The sheath 28 is preferably made from a clear, stiff but resilient plastic.

Body 30 has four fingers 35 separated by four longitudinally extending slots 36 extending from the forward end or tip 32 of body 30 to the rearward end 34. The fingers are radially arranged about a central throughbore 33 through which tube 22 may slidably pass, which throughbore 33 is in registry with and merges with base throughbore 31. The slots 36 are each adapted to receive only one of the wings 26 to allow at least part of the sheath 28 to be slid past the wings 26 to cover the needle 24. The width of each of the slots 36 is less than the width of a single wing 26 so that the arc-like fingers 35 defining the slots 36 are resiliently spread apart upon insertion of the wings 26 into the slots 36.

Tubular body 30 also includes cutouts 42 at the rearward end of the slots 36, adapted to receive and engage the wings 26 to lock the sheath in its position covering the needle. The cutouts 42 have a width approximately equal to the width of one of the wings 26 and is slightly longer in length than the length of the wings 26 so that upon receipt of the wings 26 in the slots 36, the fingers 35 will, following their resilient wedging apart, upon passage of the wings 26, snap back and assume their normal position thereby trapping the wings 26 in the cutouts 42 between the forward edges 44 and the rearward edge 48 of the cutouts and preventing the needle 24 from sliding forwardly out of the sheath 28.

Figure 3:
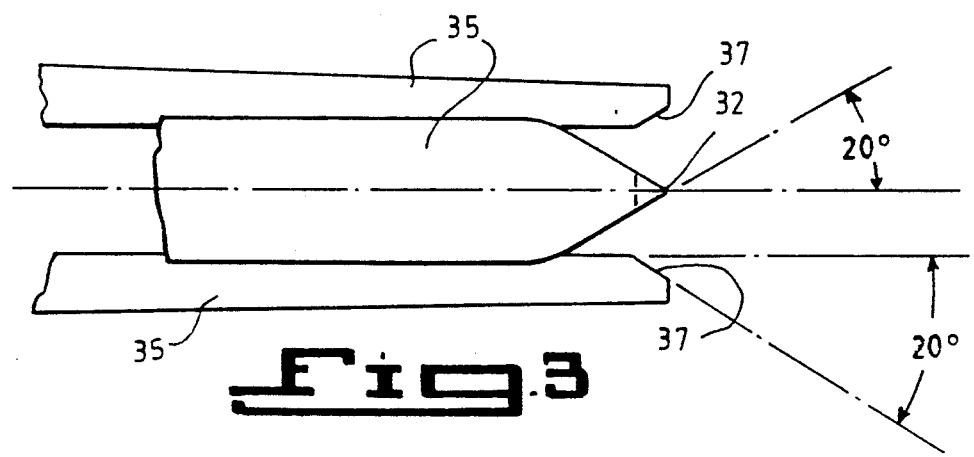
FIG. 3 is an enlarged, fragmentarily-illustrated, partially schematic side elevational view of the forward end of the slotted tubular body of the protective sheath.

As shown best in FIGS. 3, 4, and 6, the forward ends 32 of the fingers 35 are V-shaped (preferably having an included angle of 40°) and their inner edges 37 are also tapered (preferably at an angle of 20°) so that the mouth 40 of the tube widens into a plurality of V-shaped slots to facilitate the passage of the wings 26 thereinto and, in turn, into separate slots 36.

Unlike the sheath disclosed in U.S. Pat. No. 4,941,881, it is essential and imperative that the sheath includes at least three fingers 35 and slots 36 and not one or two slots as disclosed in the aforesaid patent, so as to inhibit the possibility of the two wings from being easily folded and passing through together the V-shaped mouth 40 into one of the slots 36 or causing a jam at the forward end 32 of the sheath. As can be appreciated, the use of only one slot requires the use of greater force to pull the tube 22 and the needle 24 rearwardly into the sheath 28. In addition, due to the fact that the two wings 26 are pushed into the same slot, they wedge apart the fingers of the sheath to a point whereupon they allow the tube 22 to easily escape from throughbore 33 and slot 36, thereby disengaging itself from the sheath. This is due to the fact that the tube 22 typically has a width which is less than the width of the two wings 26 together. In addition, if two fingers and two slots are used, the wings 26 will not always locate and slide into the slots without some undue manipulation on the part of the nurse, doctor or other medical personnel, as the wings may get caught up on the forward end 32 of the tubular body. In this regard, it should be realized that the wings 26 of the needle 24 having been grasped and bent in the manner shown in FIG. 1, will not always be disposed exactly 180° apart to match the 180° spaced apart slots of a "two finger" embodiment.

In contrast thereto, the present invention provides at least three fingers 35 and slots 36 so that the wings 26 will easily slide into two of the three or more slots 36. The width of each of the slots is also less than the width of one of the wings 26 which in turn is less than the width of the tube so as to prevent the tube's escape by sliding out through the slots 36. Furthermore, with the use of at least three fingers 35 and slots 36, it is not necessary to exactly align the wings 26 with the slots 36. The tapered tips 32 of the fingers 35 will easily guide the wings 26 in the mouth 40 of the tube 30 and into different slots 36 without jamming and with only a slight pulling force on the tube 22.

FIGS. 9 and 10 disclose two alternate embodiments of the sheath 28', 28", respectively, wherein FIG. 9 shows the three finger 35' alternative and FIG. 10 showing a five finger 35" alternative, in contrast to the four finger 35 embodiment of FIGS. 1–8.

In operation, the protective sheath 28 will normally be threaded onto the tubing 22 at the assembly point by the manufacturer before the butterfly needle 24, 26 is put on the tubing 22. The use of the IV infusion device 20 is no different than the use of the standard butterfly type IV infuser. The infusion device is connected to an IV apparatus and the needle is placed in the patient. The wings 26 prevent the sheath from interfering with the needle during use. When it is time to remove the IV infusion device 20 the device is removed in the same manner as a standard butterfly type IV infuser with the assistance of the wings 26.

After use by the doctor, nurse or other medical personnel, and to protect and cover a used needle, the medical professional would grasp, with one hand, the rear annular base 29 of the protective sheath and, with his other hand, pull on the tubing 22 until the butterfly wings 26 enter the mouth 40 (FIG. 7) and slide into different slots 36 until they are locked in place within the cutouts 42 at which point the needle is fully encased within the fingers 35 of the protective sheath 28 (FIG. 8). In the main embodiment of FIGS. 1–8, the wings could slide into opposite slots or adjacent slots as the case may be, and this would also apply to the three finger and five finger alternatives disclosed in FIGS. 9 and 10.

Various modifications may be made as will be apparent to those skilled in the art. For example, although the annular base is shown of reduced diameter relative to the remainder of the sheath, it could be of equal or greater diameter to suit the particular application. Similarly, although only three, four or five fingers and slots are shown, additional slots may be used to suit the particular application desired. In addition while the sheath of the present invention is preferably fabricated from injection molded plastic, it could be made from other materials or combination of materials if desired.

Accordingly, while only several embodiments of the present invention have been shown and described, it is to be understood that many changes and modifications may be made thereunto without departing from the spirit and scope of the invention as disclosed herein.

What is claimed is:

1. In an improved IV infusion set of the type including a length of tube with a hollow needle at one end, and a pair of outwardly projecting flexible wings adjacent the end of the tubing with the needle and a sheath slidably disposed on the tube and adapted to be slid over the needle to cover the needle after use, the improvement comprising:

said sheath comprising a hollow generally tubular body having a forward end oriented toward the needle and a rearward end oriented away from the needle, said body having means for more readily accommodating said wings other than 180 degrees apart when said tube is pulled through said sheath to secure said wings, said means comprising at least three longitudinally extending fingers separated by slots extending from the forward end of the body toward the rearward end, each of the slots being dimensioned to receive only one of the wings to allow at least part of said sheath to be slid past the wings to cover the needle.

2. The improved IV infusion set according to claim 1, wherein said slots each have a width which is slightly less than the width of one of said wings.

3. The improved IV infusion set according to claim 1, wherein said sheath includes means for locking the sheath in its position covering the needle to prevent needlesticks from the used needle.

4. The improved IV infusion set according to claim 3, wherein said means for locking the sheath comprising means on the sheath for engaging the wings.

5. The improved IV infusion set according to claim 4, wherein said means for locking comprises a cutout at the rearward end of each of the slots, the cutout adapted to receive and engage the wings to lock the body in its position covering the needle.

6. The improved IV infusion set according to claim 5, wherein said cutout has a width at least equal to the width of one of said wings.

7. The improved IV infusion set according to claim 1, wherein said tubular body has three fingers and three slots.

8. The improved IV infusion set according to claim 1, wherein said tubular body has four fingers and four slots.

9. The improved IV infusion set according to claim 1, wherein said tubular body has five fingers and five slots.

10. The improved IV infusion set according to claim 1, wherein said protective sheath is made from plastic.

11. The improved IV infusion set according to claim 1, wherein the forward end of said fingers are V-shaped and tapered to facilitate the passage of said wings into the slots.

12. A protecting sheath for a butterfly-type needle having a pair of wings and which is attached to a tube, comprising:

a hollow generally tubular body having a forward end and a rearward end, said body having means for more readily accommodating said winds other than 180 degrees apart when said tube is pulled through said sheath to secure said wings, said means comprising at least three longitudinally extending fingers separated by slots extending from the forward end of the body toward the rearward end, each of said slots being dimensioned to receive only one of the wings to allow at least part of said sheath to be slid past the wings to cover the needle.

13. The protecting sheath according to claim 12, wherein said slots each have a width which is slightly less than the width of one of said wings.

14. The protecting sheath according to claim 12, wherein said sheath includes means for locking the sheath in its position covering the needle to prevent needlesticks from the used needle.

15. The protecting sheath according to claim 14, wherein said means for locking the sheath comprising means on the sheath for engaging the wings.

16. The protecting sheath according to claim 15, wherein said means for locking comprises a cutout at the rearward end of each of the slots, the cutouts adapted to receive and engage the wings to lock the body in its position covering the needle.

17. The protecting sheath according to claim 16, wherein said cutout has a width at least equal to the width of one of said wings.

18. The protecting sheath according to claim 12, wherein said tubular body has three fingers and three slots.

19. The protecting sheath according to claim 12, wherein said tubular body has four fingers and four slots.

20. The protecting sheath according to claim 12, wherein said tubular body has five fingers and five slots.

* * * * *